(12) United States Patent
Cohen et al.

(10) Patent No.: US 6,551,267 B1
(45) Date of Patent: Apr. 22, 2003

(54) MEDICAL ARTICLE HAVING BLOOD-CONTACTING SURFACE

(75) Inventors: Richmond R. Cohen, Wanaque, NJ (US); Preston Keusch, Hazlet, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/691,423

(22) Filed: Oct. 18, 2000

(51) Int. Cl.[7] .............................. A61L 33/00; A61B 5/15
(52) U.S. Cl. ....................................... 604/6.15; 604/403
(58) Field of Search ................. 604/6.15, 403

(56) References Cited

U.S. PATENT DOCUMENTS

| | | |
|---|---|---|
| 4,153,739 A | 5/1979 | Kessler |
| 4,856,533 A | 8/1989 | Anraku et al. |
| 4,967,763 A | 11/1990 | Nugent et al. |
| 4,980,231 A | 12/1990 | Baker et al. |
| 4,985,026 A | 1/1991 | Kasai et al. |
| 5,171,264 A | 12/1992 | Merrill |
| 5,288,466 A | 2/1994 | Burns |
| 5,480,717 A * | 1/1996 | Kundel ........................ 428/338 |
| 5,632,776 A * | 5/1997 | Kurumatani et al. .......... 623/11 |
| 5,738,670 A * | 4/1998 | Grippi ......................... 604/403 |
| 5,824,049 A * | 10/1998 | Ragheb et al. ............. 604/53 X |
| 5,849,368 A * | 12/1998 | Hostettler et al. .......... 427/536 |
| 6,077,235 A | 6/2000 | Serpentino et al. |
| 6,299,596 B1 * | 10/2001 | Ding ........................ 604/96.01 |
| 6,299,980 B1 * | 10/2001 | Shah et al. ............... 428/423.1 |

FOREIGN PATENT DOCUMENTS

| | | |
|---|---|---|
| DE | 196 30 879 A1 | 2/1998 |
| EP | 0 787 824 A2 | 8/1997 |
| EP | 1 016 460 A2 | 7/2000 |
| WO | 96/23601 | 8/1996 |

* cited by examiner

Primary Examiner—Kevin Lee

(57) ABSTRACT

A plastic medical article, such as a catheter or blood collection tube, is coated with a crosslinked hydrogel permanently bound to the inside wall of the tube. The hydrophilic surface provided by the hydrogel prevents adherence of blood components to the surface, and the permanent adherence of the hydrogel prevents its removal by blood.

9 Claims, 2 Drawing Sheets

MEDICAL ARTICLE HAVING BLOOD-CONTACTING SURFACE

BACKGROUND OF THE INVENTION

1. Field of the Invention

This invention relates to medical articles, and more particularly, relates to an article having a hemocompatible coating permanently affixed to a blood-contacting surface of the article.

2. Background

There are many applications in the medical device industry where it is desirable that a blood-contacting surface be both compatible with blood and antithrombogenic. Exemplary of such devices is blood collection tubes. Blood samples are routinely collected in glass evacuated tubes. One end of a double-ended needle is inserted into a patient's vein. The other end of the needle then punctures a septum covering the open end of the tube so that the vacuum in the tube draws the blood sample through the needle into the tube. Using this technique, a plurality of samples can be taken using a single needle puncture of the skin.

In addition, recent advancements in analytical instrumentation have made it possible to carry out a variety of hematological or chemical diagnostic procedures on very small quantities of blood, such as may be obtained by puncture of a patient's finger, earlobe or an infant's heel. Accordingly, a variety of blood sample microcollection devices have been disclosed in the art.

Plastic tubes have been proposed for blood collection. Plastic offers a number of advantages over glass such as lower breakage, less weight in shipment, and easier disposal by incineration. However, plastics are generally hydrophobic, and blood does not flow smoothly over hydrophobic surfaces. Instead, blood components, such as platelets, fibrin or clotted blood thus generally adhere tenaciously to plastic surfaces and hang up on the walls of plastic collection tubes. This is a particular problem in small diameter gravity actuated microcollection tubes during sample collection or in vacuum tubes during subsequent centrifugation. Thus, in any collection apparatus, it is highly advantageous if the collection tube has a surface which resists adherence to blood components at any stage of the collection process or any subsequent analysis procedure.

Adherence of blood components generally is not a problem with glass articles, and accordingly, one approach to overcoming this problem in plastic has been to modify the plastic surface to be more glass-like, i.e., to present a hydrophilic surface to the blood. To this end, plastic collection tubes have been treated with a gas plasma to alter the surface chemistry by introduction of heteroatoms. In another approach, the interior wall surface of the plastic tube has been modified by coating with materials such as surface-active agents, water-soluble polymers or water insoluble polymers carrying hydrophilic coatings. For example, U.S. Pat. No. 6,077,235 discloses a blood collection tube in which permanent non-adherence is achieved by blending a hydrophilic-hydrophobic copolymer into the tube polymer.

While the above disclosures have improved blood flow and reduced adherence of blood components to plastic articles, the problem has not been totally solved because the coatings applied to the prior art surfaces are partially or completely removed by the blood so that the surfaces revert back to hydrophobic. There is a need for an article and method therefor which would prevent adherence without introducing any foreign material into the plasma, serum or clot until the intended medical procedure is complete.

SUMMARY OF THE INVENTION

A medical article having a blood-contacting surface includes a plastic substrate having a hydrogel permanently affixed to the blood-contacting surface. In this disclosure the term hydrogel is used to designate a crosslinked polymeric coating on the substrate surface, and the term hydrophilic polymer is used to designate the material which upon crosslinking gives the hydrogel.

A preferred article is an evacuated polyethylene terephthalate (PET) blood collection tube fitted with a puncturable stopper, and the preferred hydrogel is polyvinyl pyrrolidone (PVP) bound to the inside wall surface of the tube by electron beam or gamma irradiation.

The hydrogel coating becomes lubricious by absorption of water when in contact with blood, and thereby prevents blood components from adhering to the article. Because the hydrogel is permanently affixed to the article surface, it cannot be washed away by contact with the blood. Further, the coating is applied without use of any environmentally unfriendly solvents, many of which cause plastics to become cloudy and may interfere with visual or instrumental observation of the contents. Finally the article may be sterilized by the radiation used to crosslink the polymer and bind the resulting hydrogel to the substrate.

DETAILED DESCRIPTION

While this invention is satisfied by embodiments in many different forms, there will herein be described in detail preferred embodiments of the invention with the understanding that the present disclosure is to be considered as exemplary of the principles of the invention and is not intended to limit the invention to the embodiments illustrated and described. The scope of the invention will be measured by the appended claims and their equivalents.

The blood contacting article of the invention may be any device, for example, a tubing such as a catheter, obturator or stent, or any container having a closed end and an open end such as, for example, bottles, vials, flasks and the like, preferably tubes. The invention will henceforth be described in terms of the preferred tube with the understanding that the disclosure herein may equally well be applied to any other article. It is also understood that, while the invention is herein disclosed in terms of the preferred blood collection tube, the collection tube may equally well be used for collection of any other body fluid.

While the tube may be dimensioned to take a blood sample of any volume, preferred tubes are standard size as known in the art. Thus the tube may be a gravity actuated microcollection tube of conventional size, generally 40–50 mm long and 5–10 mm internal diameter. On the other hand, vacuum actuated containers designed for larger samples are generally 50 to 150 mm long and 10–20 mm in diameter. Representative conventional microcollection tubes are fully described in U.S. Pat. Nos. 4,967,763 and 5,288,466, and conventional vacuum blood collection tubes are disclosed in U.S. Pat. Nos. 4,985,026 and 4,856,533.

The drawings illustrate a vacuum blood collection tube with stopper and a gravity actuated microcollection tube with mating lip with no intention of limiting the invention to the designs shown. As is fully appreciated by one skilled in the art, the design of the collection tube and stopper is not critical, and the herein described hydrogel coating to prevent adhesion of blood components, clot and fibrin may be imparted to tubes of any design.

Figure 1:
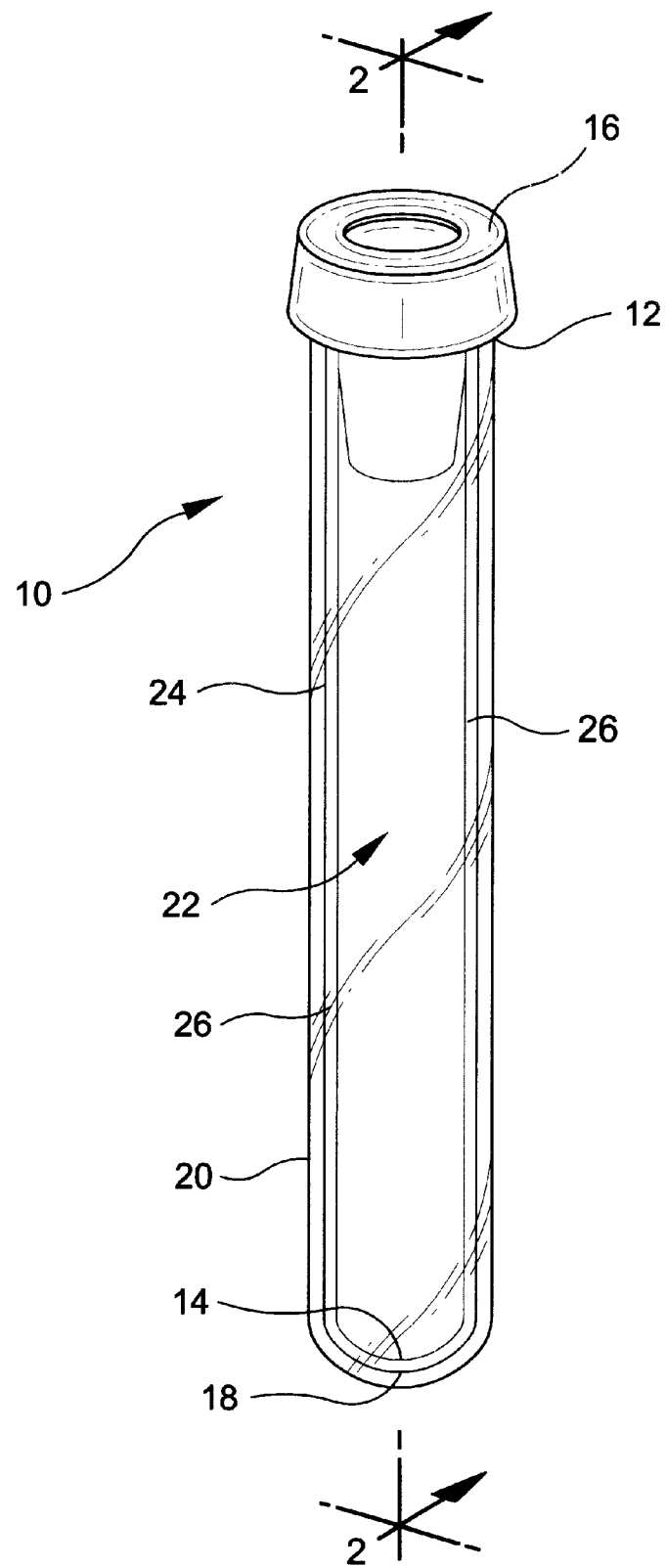
FIG. 1 is a perspective view of a typical blood collection tube with puncturable stopper.

FIG. 1 illustrates a blood collection assembly of the invention which includes a tube 10 having an open end 12, a closed end 14 and a stopper 16 in open end 12. Tube 10 has a bottom wall 18 and a side wall 20 which, together with stopper 16, enclose an interior volume 22 of the tube which preferably is evacuated. Stopper 16 is preferably puncturable and extends into and presses against the inside wall surface 24 of side wall 20 to maintain stopper 16 in place. Puncturable stoppers for evacuated sample collection tubes are standard in the art and may be made of any suitable material, such as KRATON™ (trademark of Shell Corp. for styrene-butadiene copolymer).

Figure 2:
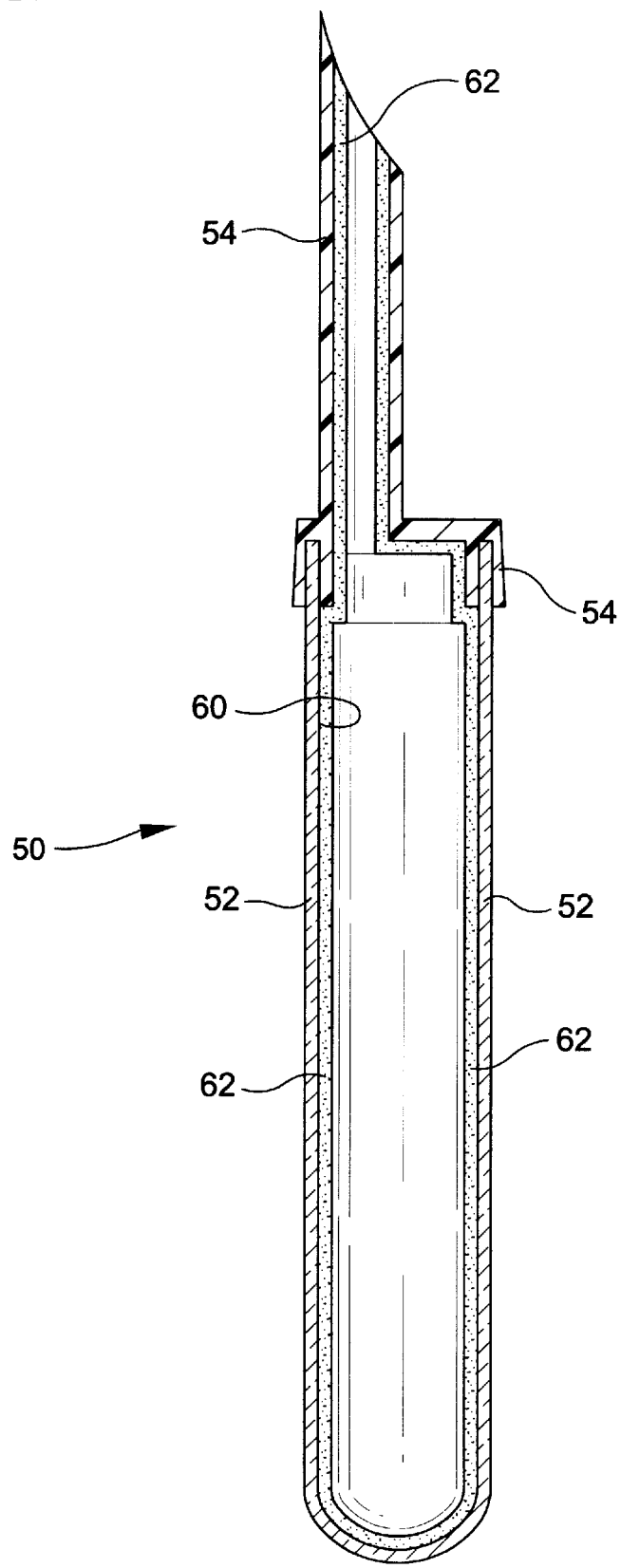
FIG. 2 is a longitudinal sectional view of a blood microcollection tube of the invention with mating lip portion.

FIG. 2 illustrates a typical microcollection assembly 50 of the invention including collection tube 52 and lip 54 to aid in directing a blood sample from a lance wound into the tube. While the drawing shows the tube and lip to be separate, they may equally well be a single integral unit consequent to the molding process and be configured to mate in sealing engagement with a closure or cap (not shown) after sample taking. Inside wall 60 of tube 52, and preferably lip 54, have thereon permanently affixed hydrogel coating 62.

Suitable tube polymers for receiving the hydrogel coating are, for example, polyolefins such as polyethylene polytetrafluoroethylene and polypropylene (PP), polyesters such as PET, polystyrene, polyurethane, polyvinylchloride, polyacrylic and mixtures or copolymers thereof. PP is preferred for microcollection tubes and PET is preferred for evacuated collection tubes.

Suitable hydrophilic polymers are polyalkyleneoxides, such as polyethyleneoxide (PEO), polypropylene oxide (PPO), PVP, polyvinyl alcohol, polyvinylacetate (PVA), polyhydroxyalkyl acrylates, polystyrene sulfonate and mixtures or copolymers thereof, such as PVP-PVA. Choice of suitable polymers for hydrogel formation is well within the purview of one skilled in the polymer arts, and no further details regarding this aspect of the invention are needed for a full understanding by one skilled in the art.

For the most preferred hydrophilic polymer, PVP, the molecular weight may be 25,000 to 2,500,000, preferably 60,000 to 2,500,000, most preferably, 900,000 to 2,500,000.

The blood collection tube of the invention may be prepared by coating the substrate with the hydrophilic polymer in water solution by any conventional method such as spraying, dipping or filling and aspirating onto the inside wall surface of the tube. In a preferred method, the hydrophilic polymer is dissolved in water at a concentration of about 2–30, preferably about 5–10% by weight, and the viscous solution applied to the substrate by wiping with an applicator sponge adapted to receive a continuous supply of the solution for an easily-automated process.

The coating on the substrate may then be partially dried by any convenient procedure which maintains the even coating, such as by a current of air or in an oven. The quantity of water rendering on the substrate after drying is not critical, and may conveniently be about 1 to 20, preferably about 2 to 10% by weight of the polymer.

After partial drying, the coating of hydrophilic polymer on the substrate may be crosslinked to give the hydrogel by any crosslinking procedure as known in the art. Preferably, crosslinking is carried out by irradiation. A dose of about 0.25 to 1.5 Mrad, preferably about 1.0 to 1.2 Mrad is generally sufficient to effect crosslinking of the PVP and bind the hydrogel to the substrate. Higher doses of radiation may be used but are generally unnecessary for permanent binding and are less economical.

Irradiation is conveniently carried out by electron beam or gamma radiation from a Cobalt 60 source.

The tube having the hydrogel bound thereto may be further processed into a standard blood collection tube by closing the open end with a puncturable septum and reducing the pressure to whatever degree of evacuation is needed to give the desired blood draw.

If it is desired to sterilize the blood collection tube, the sterilization step may also be accomplished with a 1–2 Mrad dose of radiation. It will be apparent to one skilled in the art that all three disclosed irradiation steps, i.e., crosslinking, binding and sterilizing, may be combined into one step by the proper sequence of manufacturing steps.

Any additive useful in blood analysis, including both procoagulants and anticoagulants, may be present in the blood collection assembly. In this way, the assembly, by proper selection of additive, may be used across the entire spectrum of blood collection devices. A representative, but not exhaustive list of suitable procoagulants are particulate clot activators such as silica particles and enzyme clot activators, such as elagic acid, fibrinogen and thrombin. If plasma is needed for analysis, an anticoagulant is generally provided to inhibit coagulation during centrifugation. Suitable anticoagulants are chelators such as oxalates, citrates, and EDTA or enzymes such as heparin.

The tube may contain a conventional thixotropic gel which, on centrifugation, migrates to the interface between the serum and the cells and serves for separation of the layers.

The vacuum blood collection of the invention may also be treated by any conventional methodology to enhance its resistance to the passage of moisture or gas which would reduce the tube vacuum and affect the blood draw volume. While not wishing to be limited thereby, one commonly used procedure for conferring gas and moisture impermeability is to apply a coating of siliceous material, such as SiOx, to the outside of the tube.

EXAMPLE 1

Eighty g of PVP (K120 ISP Wayne, N.J.) and 720 g of deionized water were mixed and the viscous solution was applied to the interior wall of 16×100 mm PET tubes using a 14 mm foam disc attached to a rod to give an even thin coating on the tube walls. The coated tubes were exposed to electron beam radiation from a 3.0 MeV Van de Graaff electron accelerator at doses of 0.12, 0.55, 1.0 and 4.7 Mrads to crosslink the PVP and bind it to the tube surfaces.

To ascertain the permanence of the coating, the irradiated tubes were extracted for 1 hour with water at 37° C., and the extracts were found to be free of dissolved PVP, showing the PVP to be bound to the surface.

The coated and irradiated tubes were converted to blood collection tubes by adding a conventional clot activator and serum separating gel, fitting with puncturable stoppers and evacuating. The tubes were sterilized with 1.2 Mrad gamma radiation from a Cobalt 60 source. Human blood samples were collected, after conventional clotting and centrifuging, in the tubes and, the tube surfaces were examined. No red cell or clot hangup was seen on the tube surfaces.

Serum from the blood samples collected in the tubes of the invention were used in a standard "chem screen 25" analyte study. No clinically significant differences in analyte assays were seen compared to serum controls collected in commercial evacuated blood collection tubes.

EXAMPLE 2

In the same was as described in Example 1, blood sample tubes were prepared using a 4% aqueous solution of K120 PVP. These tubes, as those of Example 1, showed no red cell or clot hangup and no appearance of PVP in the water extract.

EXAMPLE 3

In the same way as described in Example 1, blood sample tubes were prepared using a 10% aqueous solution of K90 PVP. These tubes, as those of Example 1, showed no red cell or clot hangup and no appearance of PVP in the water extract.

EXAMPLE 4

If plasma is the desired product, Example 1 maybe repeated using an anticoagulant instead of the clot activator.

COMPARATIVE EXAMPLE 5

Coated tubes were prepared as in Example 1 but not irradiated. When these tubes were subjected to the water extraction, PVP was found in the extracts.

What is claimed is:

1. A medical article comprising:
   a plastic container comprising:
   a) an open top portion, a closed bottom portion, a side wall extending from said top portion to said bottom portion and having an inner and outer surface; and
   b) a hydrogel coating disposed directly on at least a portion of said inner surface, said hydrogel being permanently bound to said surface by irradiation selected from the group consisting of electron beam or gamma so as to be impervious to removal by blood.

2. The article of claim 1 selected from the group consisting of a cup, a vial and tube.

3. The article of claim 2, wherein the container is an evacuated tube.

4. The article of claim 2 wherein said container further comprises a thrombogenic agent, an antithrombogenic agent or a serum separating gel therein.

5. The article of claim 1 wherein said plastic substrate is selected from the group consisting of a polyolefin, polyester, polystyrene, polyvinyl chloride, polyurethane, polyacrylic, polytetrafluoroethylene and copolymers and mixtures thereof.

6. The article of claim 1 wherein said hydrogel is selected from the group consisting of a crosslinked polyethylene oxide, polypropylene oxide, polyvinyl alcohol, polyvinyl acetate, polyvinyl pyrrolidone, polyhydroxyalkyl acrylate, polystyrene sulfonate and copolymers or combinations thereof.

7. A blood collection assembly comprising:
   a) an evacuated plastic tube;
   b) a puncturable stopper in said tube; and
   c) a crosslinked hydrogel coating on an inside wall surface of said tube, said coating being permanently bound to said surface by irradiation selected from the group consisting of electron beam and gamma.

8. The assembly of claim 1 further comprising a siliceous coating on the outside of said tube.

9. A method to prepare a medical container having a blood contacting surface consisting essentially of:
   a) providing a container comprising an open top portion, a closed bottom portion, a side wall extending from said top portion to said bottom portion and having an inner and outer surface
   b) coating at least a portion of the inner surface of the container with a hydrogel to give a coated surface; and
   c) irradiating said coated surface with radiation selected from the group consisting of electron beam or gamma to cause said hydrogel to bind to said inner surface.

* * * * *